United States Patent
Quintens et al.

(10) Patent No.: US 9,554,590 B2
(45) Date of Patent: Jan. 31, 2017

(54) MICROENCAPSULATED PROBIOTIC SUBSTANCE AND PROCESS OF MANUFACTURE

(75) Inventors: Johan Henri Herman Quintens, Hoegaarden (BE); Jehan Lienart Van Lidth De Jeude, Noville-sur-Mehaigne (BE); Thorsten Brandau, Karlstein (DE); Holger Strohm, Würzburg (DE); Jens Schwinn, Elsenfeld (DE)

(73) Assignees: Vesale Pharma S.A., Noville-sur-Mehaigne (BE); Brace GmbH, Alzenau (DE)

( * ) Notice: Subject to any disclaimer, the term of this patent is extended or adjusted under 35 U.S.C. 154(b) by 0 days.

(21) Appl. No.: 13/980,526

(22) PCT Filed: Jan. 20, 2012

(86) PCT No.: PCT/EP2012/050895
§ 371 (c)(1),
(2), (4) Date: Sep. 30, 2013

(87) PCT Pub. No.: WO2012/098239
PCT Pub. Date: Jul. 26, 2012

(65) Prior Publication Data
US 2014/0010918 A1    Jan. 9, 2014

Related U.S. Application Data

(60) Provisional application No. 61/503,307, filed on Jun. 30, 2011.

(30) Foreign Application Priority Data

Jan. 21, 2011   (EP) .................................... 11151686
Jan. 21, 2011   (LU) ......................................... 91782

(51) Int. Cl.
| A23L 1/30 | (2006.01) |
| A61K 9/16 | (2006.01) |
| A61K 9/19 | (2006.01) |
| A61K 9/50 | (2006.01) |
| A61K 35/741 | (2015.01) |

(52) U.S. Cl.
CPC ............ *A23L 1/3014* (2013.01); *A23L 29/256* (2016.08); *A23L 29/275* (2016.08); *A23L 29/281* (2016.08); *A23L 33/135* (2016.08); *A23P 10/30* (2016.08); *A23P 20/12* (2016.08); *A61K 9/1652* (2013.01); *A61K 9/19* (2013.01); *A61K 9/5036* (2013.01); *A61K 9/5047* (2013.01); *A61K 9/5057* (2013.01); *A61K 9/5073* (2013.01); *A61K 35/741* (2013.01); *A23V 2002/00* (2013.01); *A23Y 2220/73* (2013.01); *A23Y 2300/49* (2013.01)

(58) Field of Classification Search
CPC ....... A23L 1/3014; A61K 9/1652; A61K 9/19; A61K 9/5036; A61K 9/5047; A61K 9/5057
USPC ........................................................... 426/61
See application file for complete search history.

(56) References Cited

U.S. PATENT DOCUMENTS

| 4,888,171 A | 12/1989 | Okonogi et al. |
| 6,723,358 B1 | 4/2004 | van Lengerich |
| 2004/0247580 A1 | 12/2004 | Chung et al. |
| 2005/0153018 A1 | 7/2005 | Ubbink et al. |
| 2005/0266069 A1 | 12/2005 | Simmons et al. |
| 2006/0099247 A1* | 5/2006 | Cantwell et al. ............. 424/451 |
| 2009/0238890 A1* | 9/2009 | Piechocki et al. ............ 424/501 |
| 2010/0189767 A1 | 7/2010 | Shimoni et al. |

OTHER PUBLICATIONS

Pop, O. L. et al. Bulletin UASVM Agriculture, 69: 372-379 (2012).*
International Search Report and Written Opinion dated Mar. 2, 2012, for International Patent Application No. PCT/EP2012/050895, Applicant, Vesale Pharma SA (9 pages).

* cited by examiner

*Primary Examiner* — Hamid R Badr
(74) *Attorney, Agent, or Firm* — McCracken & Gillen LLC

(57) ABSTRACT

Dried powder solid particles are disclosed containing a probiotic microorganism and a carrier phase wherein the probiotic microorganism is encapsulated, and wherein the carrier phase further comprises at least a nutritious source. The dried powder solid particles have a particle size distribution between n and (n+400) μm, wherein n is comprised between 100 and 10,000 μm, preferably between 300 and 5000 μm, more preferably between 400 and 1000 μm.

16 Claims, No Drawings

MICROENCAPSULATED PROBIOTIC SUBSTANCE AND PROCESS OF MANUFACTURE

This present invention relates to microencapsulated probiotic substance, in particular to dried powder composition comprising solid particles containing a living probiotic microorganism and a carrier phase wherein said living probiotic microorganism is encapsulated, said carrier phase further comprising at least a nutritious source as well as an enteric composition.

Such microencapsulated probiotic substances are already known in the art. US 2010/0189767 discloses a microencapsulated probiotic substance comprising at least a probiotic substance and a first coating, comprising for example wax, shellac, resistant starch, zein protein, ethylcellulose, methylcellulose, hydroxypropyl methylcellulose, amylase acetate phthalate, cellulose acetate phthalate, hydroxyl propyl methyl cellulose phthalate, an ethylacrylate, and a methylmethacrylate in the form of a glassy matrix. Glassy matrix refers here to a matrix that is solid at room temperature and having a rigid configuration and exhibits a high elastic modulus and strength. The particle size is of at least 20 microns. This document further discloses that the weight ratio between the bacteria and the other dry components of the glossy matrix is within the range of 0.5 to 30%.

Viable and stable probiotic formulations are disclosed in the document US 2005/0266069. These formulations comprise a core of one or more probiotic bacteria, a cellulosic excipient (for example microcrystalline cellulose) and one or more additives such as disintegrants (sodium starch glycolate, alginic acid, starch, . . . ) and stabilizers (glycerol, ascorbic acid, . . . ). The core is coated with a non-enteric coating (polyvinyl alcohol, hydroxypropyl methylcellulose, hydroxypropyl cellulose, . . . ) and further coated with an enteric coating (methacrylic acid-ethyl acrylate copolymer, cellulose acetate phthalate, . . . ). The core disclosed in this document has a diameter of 100 to 1000 microns and comprises a relatively low percentage (weight percentage of the total dry weight of the core) of probiotic bacteria from 1 to 10%, 50 to 90% of microcrystalline cellulose, 0.1 to 30% of stabilizer and 0.1 to 5% of disintegrant.

The document US 2005/0153018 relates to a probiotic delivery system of particles having a size of at least 100 microns and more particularly to compacted pellets having a volume of at least 0.02 cm$^3$ and comprising viable microorganisms associated with other components such as fillers, polysaccharide binders such as hydrocolloids, plasticizer and nutritional ingredients. According to this document, the bacterial preparation is mixed with the other components in usually 0.1 to 5% of the total wet weight.

The microencapsulated probiotic substance according to the state of the art suffers from the drawbacks that the viability of the probiotic substance is limited to a few days when stored at physiological temperatures. Furthermore, despite the high survival rates of probiotic bacteria announced in these prior art documents, the number of survival probiotic bacteria is though reduced. Studies and subjective perception of consumers show that the consumption of probiotics have a number of perceived health benefits. Probiotic pharmaceutics have to be prepared, shipped and stored under refrigerated conditions, a break of the cooling chain reduces not only the activity, but also leads to enormous costs for transports and supervision of the cooling chain. The focus of this invention is to increase the viability during storage, especially focused on long term and temperature stability.

According to the definition of Fuller (1989), probiotics are live microbial feed supplements that beneficially affect the host by improving its intestinal microbial balance, whereas the World Health Organisation (WHO) defines a probiotic as live microorganisms (bacteria or yeasts), which when ingested or locally applied in sufficient numbers confer one or more specified demonstrated health benefits for the host. This well accepted knowledge leads to a large number of probiotic products on the market, ranging from nutritious drinks with probiotics over ingestive helpers, anti-acne formulations to other applications. However, the pharmaceutical formulations have altogether the problem, that they are not "consumer-friendly", as in contrary to the food products, where it is well accepted that they have to be stored in the refrigerator, pharmaceutical formulations are not accepted in the refrigerators at home, as this is "where the food is".

Most formulation developments concentrate on the application itself, as probiotics are, despite the fact that they generate lactic acid themselves, are not tolerant to the strong acid in the human or animal stomach.

It is an object of the invention to palliate at least some of these drawbacks by providing a microencapsulated probiotic substance which ensures enhanced stability of the microencapsulated probiotic substance, resulting in an elongated shelf life at high viabilities of the encapsulated probiotic substances, even at physiological or higher temperatures.

To solve this problem, the present invention provides a microencapsulated probiotic substance as mentioned in the beginning, wherein said dried powder composition presents a particle size distribution between n and (n+400) μm, wherein n is comprised between 100 and 10000 μm, preferably between 300 and 5000 μm, more preferably between 400 and 1000 μm and in that said solid particles are spherical particles comprising 50 to 80% of said living probiotic microorganism.

Therefore the present invention provides a dried powder solid particle composition that is stable during production, transport, storage and application, even at room temperature. It was shown that this novel encapsulation method ensures an elongated storage time at high viabilities of the encapsulated probiotic strains. It can also be shown that the viability is increased at elevated temperatures up to 55° C., even peak temperatures of 80° C. can be withstand by the probiotic strains under correct configuration. Indeed, it became apparent that the laminar flow drip casting method provides a narrow distribution of the size of the solid particles, which helps maintaining the viability of probiotic microorganisms having a greater resistance to high temperatures.

During production however, the probiotics are sensible, too, as they are often kept in solution for a longer time, the handling and storage can stress them.

As a very soft production method, laminar droplet generation has been used, to avoid the strong stressing during spray drying that decreases the viability. This invention shows that laminar flow drip casting, preferably with vibrational support, produces particles with high numbers of viable microorganisms and much higher survival rates than processes as spray drying, as well as a very defined size range of the resulting spheres whose surface is perfectly homogenous ("roundness"). The small size deviation and the roundness of the spherical particles have been shown to improve release characteristics and so improve the overall effect of the probiotics, the release being longer with such spherical particles in comparison with spherical particles presenting higher sizes or widely distributed sizes and a non homogenous surface.

This effect is reached by the fact the dried powder solid particles presents an evenly distribution of particle size allowing better survival rates contrarily to existing microencapsulation techniques leading to wide size distributions resulting in different protection of the beads and to false results of the survival tests. It has been surprisingly found that the vibrational drip casting process allows reaching monomodal and tightly distributed particles being even in their properties showing the overall stability that is higher than the known ones. The vibrational drip casting process is performed with a predetermined vibration amplitude and a predetermined vibration frequency at a low predetermined pressure, dictating to a predetermined speed of liquid flow. These parameters allow the obtaining of spherical particles having homogenous roundness. This is particularly advantageous since the roundness from the process used according to the invention ensures that each spherical particle exactly contains the same quantities of probiotic microorganisms and of the carrier phase. Furthermore, spherical particles being perfectly spherical present the advantages of being less sensitive to external factors such as oxidation and do not aggregate when in contact. After production, the probiotics are entrapped in the matrix of the encapsulation materials, but however, can still degrade and decompose. Therefore a further stabilisation may need to be done, which is possible by e.g. drying, freeze drying, different storage medias, spray drying etc. This invention shows that though use of the right nutritious agent, the stabilization and viability of the probiotics during freeze drying is increased as opposed to the non-stabilized ones.

Advantageously, the dried powder solid particle presents a said particle size distribution $d_{80}$ is between n and (n+200) μm wherein n is comprised between 100 and 10000 μm, preferably between 300 and 5000 μm, more preferably between 400 and 1000 μm.

Preferably, each solid particle presents an homogenous composition what means that each particle contains the same quantities of probiotic microorganisms and of the carrier phase.

In a preferred embodiment, the carrier phase comprises at least one substance chosen in the group consisting of alginate, chitosan, pectin, pullulan, gelatine, carageenan, agar.

Besides the stomach passability of the resulting particles, the particles should also disintegrate in the intestine to be released and fulfil their health mission. Thus, the right combination of shell materials has to be used. In this invention the materials have been chosen in that way that the microspheres release in the intestine after passing stomach and bile liquids, so that the survivor rate is high enough to have a clinical effect.

Preferably, said at least one substance is a hydrocolloid. The advantages of choosing such hydrocolloids as a first coating include: the non-toxicity, forms gentle gels to trap sensitive materials such as probiotic substances, the viability of the probiotic substances during the encapsulated shelf like and the reversibility of the immobilisation as the gels can be solubilised this releasing the encapsulated probiotic substances Advantageously, said nutritious source comprises at least a compound chosen in the group consisting of a monosaccharide, a polysaccharide, an aminoacid, a peptide, a protein, a vitamin, a yeast extract, a halogen salt of an alkali or earthalkali metal, an antioxidant, glycerol, zinc acetate, zinc chloride, zinc lactate, ascorbic acid, citric acids or a vegetable oil and milk fat.

In a preferred embodiment, said nutritious source is present in an amount from 0.1 to 10 wt %, preferably from 1 to 5 wt % with respect to the total weight of the microspheres before drying.

More preferably, the dried powder solid particles according to the invention comprises an external coating chosen in the group consisting of alginate, chitosan, pectin, pullulan, gelatine, carageenan, agar, cellulose, hemicellulose, ethylcellulose, carboxymethylcellulose and their mixture.

Other embodiments of the dried powder solid particles according to the invention are disclosed in the appended claims.

The invention also relates to an enteric composition comprising said dried powder solid particles according to the invention in a suitable carrier.

As aforementioned, the fact that viability is conserved during production, storage and that the probiotics are protected against temperature variation and pH attacks make the dried powder solid particles suitable for manufacturing an enteric composition with a high efficiency.

Advantageously said suitable vehicle is an enteric coating chosen in the group consisting of ethylcellulose, hydroxypropylcellulose, carboxymethylcellulose, Eudragit®, thereby rendering the enteric composition resistant to the stomach conditions for an effect in the intestinal zone.

Preferably, the enteric composition is in the form of a soft or hard gel gelating capsule, tablet, sachet and the like.

Other embodiments of the enteric composition according to the invention are mentioned in the appended claims.

The present invention relates also to a process for the manufacture of dried powder composition comprising solid particles.

Process for the manufacture of microencapsulated probiotics are known from the prior art.

For example, the document US 2005/0266069 describes a process for preparing a probiotic formulation, this process including the following steps:
dry blending a microcrystalline cellulose (MCC) with a disintegrant,
granulating the mixture of MCC and disintegrant with an aqueous dispersion comprising a lyophilized probiotic powder, stabilizers and purified water in order to form an extrudable paste,
extruding the said extrudable paste in the form of segments,
spheronizing segments to form the core of microspheres,
drying the cores to a residual moisture level, and
coating said cores to obtain microspheres.
The extrusion phase is conducted using single-screw extruder, twin-screw extruder, ram extruder or oscillating granulator.

The document US 2010/0189767 also describes a method for preparing dry microcapsules comprising probiotic microorganisms and a carbohydrate matrix, this method comprising:
providing a suspension of probiotic microorganisms,
providing a matrix comprising at least one dextrin and optionally at least one disaccharide or oligosaccharide sugar,
encapsulating the suspension of probiotic microorganisms with the matrix to obtain microcapsules, and
coating the microcapsules with a coating composition.

The encapsulation may comprise the step of fluidized bed air/N2 suspension and/or the step of ultrasonic vacuum spray drying and/or the step of spry freeze-drying.

The document US 2005/0153018 describes a process for obtaining pellets containing viable microorganisms which comprises the following steps:
- mixing a preparation of microorganisms and further components,
- drying the mixture,
- compacting the mixture under pressure to obtain pellets, and
- coating the pellets.

Unfortunately, these processes strongly reduce the viability of the probiotic microorganisms that are stressed during the extrusion step generally performed under high pressure. Furthermore, according to these processes, it is difficult to obtain microspheres presenting the same roundness and homogenous surfaces.

To overcome this problem, another object of the present invention concerns a process for the manufacture of dried powder composition comprising solid particles under the form of spherical particles comprising the following steps:
- mixing a preparation of living probiotic microorganisms and a carrier phase comprising at least a nutritious source,
- extruding the mixture of said living probiotic microorganisms and said carrier phase to produce microspheres, and
- collecting said microspheres into a bath containing a solidification solution.

This process is characterized in that said extrusion step is performed at a predetermined speed of liquid flow of 0.2 to 5 m/s through at least one vibrating nozzle in a laminar flow drip casting to obtain said dried powder particles under the form of spherical particles, said vibrating nozzle having a vibration frequency in a range of 1 to 20000 Hz and a vibration amplitude of at least 0.5 μm.

This process constitutes a very soft production method based on laminar droplet generation to avoid the strong stressing during the extrusion step that decreases the viability of the probiotic microorganisms. The speed of liquid flow of 0.2 to 5 m/s corresponds to a process pressure on a BRACE Spherisator device of 200 to 800 mBar. This process provides a narrow distribution of the size of the solid particles, which helps maintain the viability of probiotic microorganisms having a greater resistance to high temperatures. Also, this process provides spherical particles having homogenous roundness.

Preferably, according to the present invention, the laminar flow drip casting from at least one vibrating nozzle is obtained with a vibrational support.

Advantageously, vibration of the vibrating nozzle is orientated in an axial or a lateral direction with respect to the flow to generate droplets.

Preferably, according to the present invention, the produced spherical particles have a diameter in the range of 100 to 10000 μm.

Advantageously, according to the present invention, two liquids are extruded in a laminar flow with one or multiple double nozzle systems comprising an inner nozzle and an outer nozzle. In this case, two liquids are extruded in a laminar flow with at least one double nozzle system consisting in an inner nozzle and an outer nozzle, the said outer nozzle having at least the same diameter as the inner nozzle. The inner liquid is then the forming the core while the outer liquid is later forming the shell. The use of such nozzles is advantageous since it allows producing core-shell encapsulation (or micro-granulation or matrix-encapsulation): the core material is completely isolated from the surrounding environment, giving it perfect protection. The shell material can have, for example, gas barriers, diffusion barriers or colorants.

Preferably, according to the present invention, the process for the manufacture of dried powder composition comprising solid particles comprises an additional step being the encapsulation of the extruded mixture.

Advantageously, the process for the manufacture of dried powder composition comprising solid particles according to the present invention comprises an external coating additional step.

Other details and advantages of the microencapsulated probiotic according to the invention will become apparent from the description of preferred embodiments of the invention by way of non limiting examples.

Example 1

Alginate-EC Beads and Probiotics Paste

Microspheres of *L. Rhamnosus* in a matrix made of alginate and with an ethylcellulose external coating have been made with the following protocole:

150 g of *L. Rhamnosus* paste ($5 \times 10^{10}$ cfu) was dispersed in 150 g of sterile NaCl solution (0.85% w/w NaCl) to prepare a *L. Rhamnosus* suspension.

150 g of a 5% w/w sterile alginate solution was added to 300 g of the *L. Rhamnosus* suspension Drip casting with a laminar flow break-up unit was performed to produce 800 μm microspheres by solidification in a 4% w/w $CaCl_2$ solution. The separation and washing of the microspheres was done in 0.85% w/w NaCl solution.

400 g of microspheres were stirred for 1 minute in 400 g of a solution of 1% w/w ethyl cellulose in Ethanol to produce the ethylcellulose coating (EC coating). The separation and washing of the coated microsphere was done in 0.85% w/w NaCl solution. 380 g of microspheres were stored in 380 g of a sterile aqueous solution of 5% w/w glucose before freeze drying in said glucose storage solution. A dry free flowing powder of microspheres of 700-900 μm in diameter was obtained.

Example 2

Alginate-Gelatin Beads and Probiotic Paste

Microspheres of *L. Rhamnosus* in a matrix of alginate and with a gelatine coating has been made following the under mentioned protocol:

200 g of *L. Rhamnosus* paste ($5 \times 10^{10}$ cfu) was dispersed in 200 g of sterile NaCl solution (0.85% w/w NaCl) to prepare a *L. Rhamnosus* suspension.

200 g of a 5% w/w sterile alginate solution was added to 400 g of the *L. Rhamnosus* suspension Drip casting with a laminar flow break-up unit was performed to produce 500 μm microspheres by solidification in a 5% w/w calcium lactate solution.

The separation and washing of the microspheres was done in 0.85% w/w NaCl solution.

550 g of microspheres were stirred for 1 h in 550 g of a 5% w/w gelatin solution for producing the crosslinked gelatine coating.

The microspheres were then stirred for 2 minutes in 550 g of a 10% w/w glutaraldehyde solution. The separation and washing of the coated microspheres was done in 0.85% w/w NaCl solution.

550 g of microspheres were stored in 550 g of a sterile aqueous solution of 10% w/w maltodextrin before freeze drying in the maltodextrin storage solution:

A dry free flowing powder of microspheres of 400-600 µm in diameter was obtained.

Example 3

Alginate-CMC-Gelatin Beads with Probiotic Paste

Microspheres of *L. Rhamnosus* in a matrix of alginate and with a carboxy methylcellulose coating and a gelating crosslinked coating have been made as follows:

300 g of *L. Rhamnosus* paste ($5 \times 10^{10}$ cfu) was dispersed in 150 g of sterile NaCl solution (0.85% w/w NaCl) to prepare a *L. Rhamnosus* suspension.

75 g of a 10% w/w sterile alginate solution was added to 450 g of the *L. Rhamnosus* suspension Drip casting with a laminar flow breakup unit was performed to produce 1000 µm microspheres by solidification in a 3% w/w calcium gluconate solution. The separation and washing of the microsphere was done in 0.85% w/w NaCl solution 500 g of microspheres were stirred for 10 minutes in 500 g of an aqueous solution of 2% carboxymethylcellulose. The coated microspheres have further been separated and washed in 0.85% w/w NaCl solution.

500 g of microspheres were further stirred for 1 h in 500 g of a 5% w/w gelatin solution, to produce the crosslinked gelatine coated on the microspheres.

The microspheres were then stirred for 2 minutes in 500 g of a 10% glutaraldehyde solution and separated and washed in 0.85% w/w NaCl solution.

500 g of microspheres were stored in 500 g of a sterile aqueous solution of 10% w/w glycerol and freeze dryed in the glycerol storage solution:

A dry free flowing powder of microspheres of 800-1200 µm in diameter was obtained.

Example 4

Gelatin-Guar Gum-CMC-Beads with Probiotic Paste

Microspheres of *Bifidobacterium Lactis* in a matrix of gelatine, coated with guar gum and carboxymethylcellulose have been made as follows:

200 g of *Bifidobacterium Lactis* paste was dispersed in 100 g of sterile NaCl solution (0.85% w/w NaCl) to prepare a *Bifidobacterium Lactis* in suspension.

150 g of a sterile 30% gelatin solution was added to 300 g of the *Bifidobacterium Lactis* suspension at 37° C.

Drip casting with a laminar flow breakup unit was performed to produce 1000 µm microspheres by soldification in caprylic/capric triglyceride at 5° C. The separation and washing of the microsphere was done in 0.85% w/w NaCl solution.

400 g of microspheres were stirred for 10 minutes in 400 g of an aqueous solution of 5% w/w guar gum to produce the coated microspheres with guar gum. The coated microsphere were then separed and washed in 0.85% w/w NaCl solution.

400 g of microspheres were stirred for 10 minutes in 400 g of an aqueous solution of 2% carboxymethylcellulose for building the CMC coating. The microspheres were then separated and washed in 0.85% w/w NaCl solution.

400 g of microspheres were stored in 400 g of a sterile aqueous solution of 4% w/w glycerol before freeze drying in this glycerol storage solution:

A dry free flowing powder of microspheres of 800-1200 µm in diameter was obtained.

Example 5

Alginate-Chitosan-Gelatin Beads with Probiotic Paste

Microspheres of *L. Rhamnosus* in a matrix of alginate and wjtb a chitosan coating with further gelatine coating was made as follows:

400 g of *L. Rhamnosus* paste ($5 \times 10^{10}$ cfu) was dispersed in 200 g of sterile NaCl solution (0.85% w/w NaCl) to prepare a *L. Rhamnosus* suspension.

100 g of a 10% sterile alginate solution was added to 600 g of the *L. Rhamnosus* suspension.

Drip casting with a laminar flow breakup unit was performed to produce 1000 µm microspheres by soldification in a 2% w/w CaCl$_2$ solution. The separation and washing of the microspheres was done in 0.85% w/w NaCl solution.

600 g of microspheres were stirred for 10 minutes in 1200 g of an aqueous solution of 1% w/w chitosan for manufacturing chitosan coated microspheres. The separation and washing of the coated microspheres was done in 0.85% w/w NaCl solution.

600 g of microspheres were stirred for 1 h, in 1200 g of a 5% w/w gelatin solution to further coat the microsphere with gelatine. The separation and washing of the coated microspheres was done in 0.85% w/w NaCl solution.

600 g of microspheres were stored in 600 g of a sterile aqueous solution of 4% w/w glycerol before freeze drying in the glycerol storage solution:

A dry free flowing powder of microspheres of 800-1200 µm in diameter was obtained.

Example 6

Alginate Beads with Probiotic Paste

Microspheres of *L. Rhamnosus* in a matrix of alginate has been made as follows:

200 g of *L. Rhamnosus* paste ($5 \times 10^{10}$ cfu) was dispersed in 150 g of a sterile solution of 6.7% w/w polysaccharide and 0.85% w/w NaCl to form a *L. Rhamnosus* suspension.

230 g of a 3% w/w sterile alginate solution was added to 350 g of the *L. Rhamnosus* suspension.

Drip casting with a laminar flow breakup unit was performed to produce 1000 µm microspheres by solidification in a 2% w/w CaCl$_2$ solution. The separation and washing of the microspheres was done in 0.85% w/w NaCl solution.

550 g of microspheres were stored in 550 g of a sterile aqueous solution of 5% w/w glucose and 3% w/w glycerol before freeze drying in the glycerol storage solution:

A dry free flowing powder of microspheres of 400-900 µm in diameter was obtained.

The enumeration of the viable bacteria in microspheres is made as follows:

Two samples were prepared with the alginate *L. Rhamnosus* microsphere, one from the dried powder and one in a wet state:

Sample 1: *Lactobacillus rhamnosus* microspheres, diameter ca 400-900 microns, dried with glucose/glycerol.

Sample 2: *Lactobacillus rhamnosus* microspheres, diameter ca 800-1200 microns, wet in glucose/glycerol solution.

The Microspheres have to be dissolved before enumeration of viable bacteria. Dissolution procedures were adapted to differences during the drying stage of the microspheres:

Sample 1 has been prepared by aseptically weighing 100 mg of dried microspheres to a 15 ml conical sterile tube and adding 2.9 ml Na citrate 0.1M. The mixture is vortexed for 15 minutes (dilution 30×).

Sample 2 has been prepared by first separating the microspheres from the storage solution (glucose/glycerol solution) with a sterile sieve (whatman filter paper). 100 mg of wet microspheres were added to a 15 ml conical sterile tube with 1.9 ml Na citrate 0.1M. The mixture is vortexed for 3 minutes (dilution 20×)

Sample dissolution was made in duplicate for both samples.

15 ml of the MRS agar have been poured approximately into each plate and allowed for solidification at room temperature on a cool level surface.

In sterile tubes filled with sterile 9 ml 0.1% peptone dilution blanks 1 ml of the primary dilution (from the conical tube) is added to the 9 ml of diluent with a 1 ml pipette so as to obtain a $10^{-1}$ dilution. This operation is repeated until the desired dilution series is obtained. Dilution tubes shaked as stated in standard Methods for the examination of dairy products The experiments are made in triplicate. 0.1 ml of each appropriate dilution is transferred on the surface of labelled, sterile Petri plates poured with circa 15 ml MRS agar nutrient medium. The plates were incubated at 35° C. for minimum 72 hours till 144 hours.

Count colonies on the MRS agar plates and record as viable *Lactobacillus rhamnosus* cell count per gram, taking into account the dilution factor of the counted plates. Only plates having between 25 and 250 colonies should be counted. (See Standard methods for the examination of dairy products, 16$^{th}$ edition, pages 213-246).

Results
Initial Weigh:
Sample 1: duplicate 1: 100 mg duplicate 2: 103 mg Average: 101.5 mg.
Sample 2: duplicate 1: 102 mg duplicate2: 99 mg Average: 100.5 mg
Initial Dilution Rate:
Sample 1: 101.5 mg in 2.9 ml=dilution 29.6×.
Sample 2: 100.5 mg in 1.9 ml=dilution 19.9×
Count cfu (Colony-Forming-Unit):

| | Dilution $10^{-5}$ | | | Dilution $10^{-4}$ | | | Dilution $10^{-3}$ | | | Dilution $10^{-2}$ | |
|---|---|---|---|---|---|---|---|---|---|---|---|
| Replication | 1 | 2 | 3 | 1 | 2 | 3 | 1 | 2 | 3 | 1 | 2 |
| Sample 1 | | | | | | | | | | | |
| Duplicate 1: | 3 | 6 | 1 | 18 | 6 | 19 | 299 | 192 | 279 | > | > |
| Duplicate 2: | 1 | 1 | 1 | 17 | 12 | 16 | 151 | 114 | 160 | > | > |
| Sample 2 | | | | | | | | | | | |
| Duplicate 1: | 8 | 6 | 8 | 32 | 88 | 52 | — | 171 | 203 | > | > |
| Duplicate 2: | — | 8 | 6 | 35 | 85 | 39 | — | ? | 123 | > | > |

The Results of the Enumeration is as Follows:
Sample 1: $192.10^3 \times 29.6 = 5.68 \ 10^6$ cfu/g microspheres (dry weight)
Sample 2: $635.10^3 \times 19.9 = 1.26 \ 10^7$ cfu/g microspheres (wet weight)

As it can be seen, with a correct choice of diameter and nutrious agent, a survival rate of 1:1000 can be achieved during all processing. While the larger diameter preserves a higher number of living cells through the process, the yield of living microorganisms of more than $1.10^7$ cfus is sufficient for a probiotic effect.

Example 7

Alginate-CMC-Gelatin Beads with Lyophilised Probiotics

Microspheres of *L. rhamnosus* in an alginate matrix coated with carboxymethylcellulose and gelatine has been manufactured as follows:

150 g of lyophilized *L. rhamnosus* powder ($8.8 \times 10^{11}$ cfu/g) was dispersed in 300 g of sterile NaCl solution (0.85% w/w NaCl) to form a *L. rhamnosus* suspension. The *L. rhamnosus* provided are therefore $1.32.10^{14}$ cfu in 150 g.

75 g of a 10% w/w sterile alginate solution was added to 450 g of the *L. rhamnosus* suspension Drip casting with a laminar flow breakup unit was performed to produce 1000 μm microspheres by solidification in a 3% w/w calcium gluconate solution. The separation and washing of the microspheres was done in 0.85% w/w NaCl solution.

500 g of microspheres were stirred for 10 minutes in 500 g of an aqueous solution of 2% w/w carboxymethylcellulose to obtain the CMC coating. The separation and washing of the microspheres was done in 0.85% w/w NaCl solution.

Further, 500 g of microspheres were stirred for 1 h, in 500 g of a 5% w/w gelatin solution, and the microspheres were then stirred for 2 minutes in 500 g of a 10% w/w glutaraldehyde solution for reaching a crosslinked gelatine coating. The separation and washing of the microspheres was done in 0.85% w/w NaCl solution.

500 g of microspheres were stored in 500 g of a sterile aqueous solution of 10% w/w glycerol before freeze drying in storage solution. After double coating and crosslinking which do not absorb all coating material but only a small quantity of 0.1-1%, the spheres have been dried and 50 g of glycerol was added (500 g of 10% w/w glycerol), yielding to a dry matter of 203.93 g, under the form of a dry free flowing powder of microspheres of 800-1200 μm in diameter with a cell count of $2.9 \times 10^{11}$ cfu/g was obtained. This means that from the $1.32.10^{14}$ cfu engaged from the lyophilized *L. rhamnosus*, it still remains $0.61.10^{14}$ cfu ($203.93 \ g. \ 2.9.10^{11}$). Consequently, the yield of the living probiotics is about 50% being drastically higher than with the process of the prior art.

Example 8

Alginate-EC Beads with Lyophilised Probiotics

Microspheres of *L. rhamnosus* in an alginate matrix coated with ethylcellulose has been manufactured as follows:

67.5 g of lyophilized *L. rhamnosus* powder ($8.8 \times 10^{11}$ cfu) were dispersed in 217.5 g of sterile NaCl solution (0.85% w/w NaCl) to prepare a suspension of *L. rhamnosus*.

150 g of a 5% sterile alginate solution was added to 300 g of the *L. rhamnosus* suspension;

Drip casting with a laminar flow breakup unit was performed to produce 800 μm microspheres by solidification in a 4% w/w $CaCl_2$ solution. The separation and washing of the microspheres was done in 0.85% w/w NaCl solution.

Further, 400 g of microspheres were stirred for 1 minute in 400 g of a solution of 1% w/w ethyl cellulose in ethanol to prepare EC coated microspheres separation and washing of the microspheres are made in 0.85% w/w NaCl solution.

380 g of microspheres were stored in 380 g of a sterile aqueous solution of 5% w/w glucose before freeze drying in the glucose storage solution:

96.32 g of a dry free flowing powder of microspheres of 700-900 μm in diameter with a cell count of $1.9 \times 10^{11}$ cfu was obtained. That means that from the $5.94.10^{13}$ cfu engaged at the first step, there remains $1.8310^{13}$ cfu of $(8.8.10^{11} \times 67.5)$ living probiotics $(96.32 \times 1.910^{11})$ corresponding to about 31% of probiotics kept alive.

Example 9

Alginate-Gelatin Beads with Lyophilised Probiotics

Microspheres of *L. rhamnosus* in an alginate matrix coated with gelatine has been manufactured as follows:

100 g of lyophilized *L. rhamnosus* powder $(8.8 \times 10^{11}$ cfu) was dispersed in 300 g of sterile NaCl solution (0.85% w/w NaCl) to form a *L. rhamnosus* suspension. The probiotics engaged therefore of $8.8.10^{13}$ cfu for preparing the alginate gelatine beads.

200 g of a 5 w/w sterile alginate solution was added to 400 g of the *L. rhamnosus* suspension.

Drip casting with a laminar flow breakup unit was performed to produce 500 μm microspheres by solidification in a 5% w/w calcium lactate solution. The separation and washing of the microspheres was done in 0.85% w/w NaCl solution.

550 g of microspheres were stirred for 1 h, in 550 g of a 5% w/w gelatin solution for obtaining a crosslinked gelatine coating.

The microspheres were then stirred for 2 minutes in 550 g of a 10% w/w glutaraldehyde solution. The separation and washing of the microspheres was done in 0.85% w/w NaCl solution.

550 g of the microspheres were stored in 550 g of a sterile aqueous solution of 10% maltodextrin before freeze drying in the maltodextrin storage solution:

168.25 g of a dry free flowing powder of microspheres of 400-600 μm in diameter with a cell count of $8.5 \times 10^{10}$ cfu was obtained, corresponding to $1.4310^{13}$ cfu in the 168.25 g. As conclusion, an alginate-gelatine microcapsule with a crosslinked coating has a substantially high number of surviving microorganisms, essentially for a commercial viable process since the ration of probiotics kept alive is 16.25 yielding to a powder containing $8.910^{10}$ cfu (largely greater than $10^7$ cfu required).

Example 10

Gelating-Guar Gum-CMC Beads—Lyophilised Probiotic

Microspheres of *Bifidobacterium lactis* in a matrix of gelatine coated with guar gum and carboxymethylcellulose was prepared as follows:

100 g of lyophilized *Bifidobacterium lactis* powder was dispersed in 200 g of sterile NaCl solution (0.85% w/w NaCl) to prepare a *Bifidobacterium lactis* suspension.

150 g of a sterile 30% w/w gelatin solution was added to 300 g of *Bifidobacterium lactis* suspension at 37° C.

Drip casting with a laminar flow breakup unit was performed to produce 1000 μm microspheres by solidification in caprylic/capric triglyceride at 5° C. The separation and washing of the microspheres was done in 0.85% NaCl solution.

400 g of microspheres were stirred for 10 minutes in 400 g of an aqueous solution of 5% w/w guar gum to coat the microspheres with guar gum and the separation and washing of the microspheres is carried out in 0.85% w/w NaCl solution.

400 g of microspheres were stirred for 10 minutes in 400 g of an aqueous solution of 2% w/w carboxymethylcellulose to coat the microspheres with CMC and the separation and washing of the microspheres is carried out in 0.85% w/w NaCl solution.

400 g of microspheres were stored in 400 g of a sterile aqueous solution of 4% w/w glycerol before freeze drying in the glycerol storage solution:

A dry free flowing powder of microspheres of 800-1200 μm in diameter with a cell count of $2.9 \times 10^{11}$ cfu was obtained being higher than the $10^7$ value required for such application.

A conclusion it was shown that the carboxy methyl cellulose coating with glycerol as nutritious source during freeze drying yields very high survival rates in an enteric microsphere.

Example 11

Alginate-Chitosan-Gelatin Beads with Lyophilised Probiotics

Microspheres of *L. rhamnosus* in an alginate matrix coated with chitosan and gelatine has been manufactured as follows:

200 g of lyophilized *L. rhamnosus* powder $(8.8 \times 10^{11}$ cfu) was dispersed in 400 g of sterile NaCl solution (0.85% w/w NaCl) to form a *L. rhamnosus* suspension $(1.76.10^{14}$ cfu of *L. rhamnosus* engaged).

100 g of a 10% sterile alginate solution was added to 600 g of the *L. rhamnosus* suspension.

Drip casting with a laminar flow breakup unit was performed to produce 1000 μm microspheres by solidification in a 2% w/w $CaCl_2$ solution. The separation and washing of the microspheres was carried out in 0.85% w/w NaCl solution.

600 g of microspheres were stirred for 10 minutes in 1200 g of an aqueous solution of 1% w/w chitosan and the separation and washing of the microspheres was carried out in 0.85% w/w NaCl solution.

600 g of microspheres were further stirred for 1 h, in 1200 g of a 5% w/w gelatin solution and the separation and washing of the microspheres was carried out in 0.85% w/w NaCl solution.

600 g of microspheres were stored in 600 g of a sterile aqueous solution of 4% w/w glycerol before freeze drying in the glycerol storage solution:

238.8 g of a dry free flowing powder of microspheres of 800-1200 μm in diameter with a cell count of $2.9 \times 10^{11}$ cfu was obtained, corresponding to a total of $0.69 \times 10^{14}$ cfu (yield of living probiotics=39.3%).

As conclusion, it was shown that the chitosan coating with glycerol as nutritious source during freeze drying yields very high survival rates in an enteric microsphere.

Example 12

Alginate Beads with Lyophilized Probiotics 75 g of lyophilized *L. rhamnosus* powder was dispersed in 250 g of a sterile solution of 3.6% w/w polysaccharide and 0.85% w/w NaCl to form a *L. rhamnosus* suspension.

175 g of a 5% w/w sterile alginate solution was added to 325 g of the *L. rhamnosus* suspension Drip casting with a laminar flow breakup unit was performed to produce 1100 μm microspheres by solidification in a 2% w/w $CaCl_2$ solution. The separation and washing of the microspheres is carried out in 0.85% w/w NaCl solution.

450 g of microspheres were stored in 450 g of a sterile aqueous solution of 5% w/w glucose.

The enumeration made as previously described reveals $8.1\ 10^9$ cfu/g microspheres wet weight. A content of $1.87.10^{11}$ cfu/g was present in the lyophilised powder, instead of the $45.10^{11}$ declared. As the starting lyophilized powder represents 15% of the total weight of the wet microspheres, this content corresponds to $(8.1.10^9 \times 100)\ \%\ 15 = 5.4 \times 10^{10}$ cfu/g equivalent powder.

Example 13

Alginate Beads with Freeze Dried *Bifidobacterium lactis*

The following mixtures were prepared:
7.5% of *B. lactis* (Bifido 300 B—lyophilized probiotic powder *Bif. Lactis*)
1.5% alginate at a concentration of 5% w/w
89.5% NaCl solution at a concentration of 0.85% w/w
1.5% of one of the following additive used as carriers
  Brace Mix=pullulan
  Starch 1
  Starch 2
  Dextrin
  Na CML Cellulose (CMC)
  Hydroxypropyl methylcellulose (HPMC)
  Microcrystalline cellulose (MC)

Drip casting with laminar flow breakup unit was performed to produce 1100 μm microspheres by solidification in a 4% w/w $CaCl_2$ solution. The separation and washing of the microspheres is carried out in 0.9% w/w NaCl solution.

Microspheres were then directly plated (fresh beads) for CFU count or were frozen in nitrogen at −196° C. and then freeze dried at −50° C. before being plated (dried beads) for CFU count. After incubation at 37° C. during 72 h, CFU was determined for fresh beads and dried beads, as previously described.

The results obtained are presented in the Table below.

| Sample | Form | Cell count (average CFU/gram) |
| --- | --- | --- |
| Brace Mix | Fresh | $3.43 \times 10^{14}$ |
|  | Dried | $3.3 \times 10^{11}$ |
| HPMC | Fresh | $1.9 \times 10^{12}$ |
|  | Dried | $8.2 \times 10^{11}$ |
| CMC | Fresh | $1.5 \times 10^{10}$ |
| MC | Fresh | $3.7 \times 10^{09}$ |
| Starch 1 | Fresh | $4.1 \times 10^{09}$ |
| Starch 2 | Fresh | $3.8 \times 10^{09}$ |
| Dextrin | Fresh | $2.9 \times 10^{06}$ |

The CFU count made as previously described reveals that Brace Mix (fresh and dried forms), HPMC (fresh and dried forms), CMC (fresh form), MC (fresh form), Starch 1 (fresh form) and Starch 2 (fresh form) used as carriers (1.5% of the mixture) ensure a viability of *B. lactis* (7.5% of the mixture) of at least $10^{09}$ CFU/gram.

The invention claimed is:

1. A dried powder composition comprising solid particles containing:
   a) a probiotic microorganism,
   b) a carrier phase wherein said probiotic microorganism is encapsulated, said carrier phase further comprising at least a nutritious source as well as an enteric composition,
   wherein said dried powder composition presents a particle size distribution between n and (n+400) μm, wherein n is comprised between 100 and 10,000 μm, and said solid particles are spherical particles comprising 50 to 80 wt. % of said probiotic microorganism, and wherein said carrier phase comprises a mixture of alginate and pullulan.

2. The dried powder solid particles according to claim 1, wherein said particle size distribution is between n and (n+200) μm wherein n is comprised between 100 and 10,000 μm.

3. The dried powder solid particles according to claim 1, wherein each of the solid particles presents a homogeneous composition.

4. The dried powder solid particles according to claim 1, wherein said nutritious source comprises at least a compound selected from the group consisting of a monosaccharide, a polysaccharide, an aminoacid, a peptide, a protein, a vitamin, a yeast extract, a halogen salt of an alkali or earthalkali metal, an antioxidant, glycerol, zinc acetate, zinc chloride, zinc lactate, ascorbic acid, citric acids or a vegetable oil and milk fat.

5. The dried powder solid particles according to claim 1, wherein said nutritious source is present in an amount from 1 to 5 wt. % with respect to the total weight of the dried powder solid particles.

6. The dried powder solid particles according to claim 1, further comprising an external coating selected from the group consisting of alginate, chitosan, pectin, pullulan, gelatine, carageenan, agar, cellulose, hemicellulose, ethylcellulose, carboxymethylcellulose and their mixture.

7. The enteric composition comprising said dried powder solid particles according to claim 1 in a suitable vehicle.

8. The enteric composition according to claim 7, wherein said suitable vehicle is an enteric coating selected from the group consisting of ethylcellulose, hydroxypropylcellulose, carboxymethylcellulose, and methacrylic acid-ethyl acrylate copolymer.

9. The enteric composition according to claim 7, in the form of a soft or hard capsule, tablet, or sachet.

10. A process for the manufacture of dried powder composition comprising solid particles containing a probiotic microorganism in the form of spherical particles comprising the following steps:
   mixing a preparation of probiotic microorganisms and a carrier phase comprising at least a nutritious source,
      wherein the carrier phase comprises at least one substance selected from the group consisting of alginate, chitosan, pectin, pullulan, gelatine, carrageenan, agar, and
      wherein said nutritious source comprises at least a compound selected from the group consisting of a monosaccharide, a polysaccharide, an aminoacid, a peptide, a protein, a vitamin, a yeast extract, a halogen salt of an alkali or earthalkali metal, an antioxidant, glycerol, zinc acetate, zinc chloride, zinc lactate, ascorbic acid, citric acids or a vegetable oil and milk fat,
   extruding the mixture of said probiotic microorganisms and said carrier phase to produce microspheres, and
   collecting said microspheres into a bath containing a solidification solution, and wherein said extrusion step is performed at a predetermined speed of liquid flow of 0.2 to 5 m/s through at least one vibrating nozzle in a laminar flow drip casting to obtain said dried powder particles under the form of spherical particles, said vibrating nozzle having a vibration frequency in a range of 1 to 20,000 Hz. and a vibration amplitude of at least 0.5 μm.

11. The process according to claim 10, wherein the laminar flow drip casting from at least one vibrating nozzle is obtained with a vibrational support.

12. The process according to claim 10, wherein the vibration of the vibrating nozzle is orientated in an axial or a lateral direction with respect to the flow to generate droplets.

13. The process according to claim 10, wherein the said produced spherical particles have a diameter in the range of 100 to 10,000 μm.

14. The process according to claim 10, wherein two liquids are extruded in a laminar flow with one or multiple double nozzle systems comprising an inner nozzle and an outer nozzle.

15. The process according to claim 10, further comprising an additional step of encapsulating the extruded mixture.

16. The process according to claim 10, further comprising an external coating step.

* * * * *